United States Patent [19]

Stanley et al.

[11] Patent Number: 4,671,953
[45] Date of Patent: Jun. 9, 1987

[54] METHODS AND COMPOSITIONS FOR NONINVASIVE ADMINISTRATION OF SEDATIVES, ANALGESICS, AND ANESTHETICS

[75] Inventor: Theodore H. Stanley, Salt Lake City; Brian Haque, West Valley City, both of Utah

[73] Assignee: University of Utah Research Foundation, Salt Lake City, Utah

[21] Appl. No.: 729,301

[22] Filed: May 1, 1985

[51] Int. Cl.⁴ .......................... A61J 3/08; A61K 9/20; A61K 31/445

[52] U.S. Cl. .................................... 424/440; 514/317; 514/777; 514/948; 426/104; 426/660; 426/801

[58] Field of Search .................. 424/18; 514/948, 317, 514/777

[56] References Cited

U.S. PATENT DOCUMENTS

| | | | |
|---|---|---|---|
| 109,677 | 11/1970 | Seitz . | |
| 1,430,642 | 10/1922 | Gross | 99/138 |
| 1,593,858 | 7/1926 | Venable | 99/138 |
| 1,847,415 | 3/1932 | Snell | 99/138 |
| 1,915,614 | 6/1933 | Parker | 99/138 |
| 1,971,560 | 8/1934 | Guyon | 90/16 |
| 2,096,611 | 10/1937 | Ellestad | 99/138 |
| 2,208,120 | 7/1940 | Coleman | 167/82 |
| 2,246,778 | 6/1941 | Cahoon | 99/138 |
| 2,295,042 | 9/1942 | Llewellyn | 43/34 |
| 2,323,656 | 7/1943 | Helfenstein | 43/36 |
| 2,388,533 | 11/1945 | Edmondson et al. | 128/202 |
| 2,469,589 | 5/1949 | Barricini | 99/138 |
| 2,488,272 | 11/1949 | Davis | 57/154 |
| 2,499,734 | 3/1950 | Edmondson et al. | 128/197 |
| 2,508,560 | 5/1950 | Adams | 43/36 |
| 2,553,446 | 5/1951 | Edmondson et al. | 128/188 |
| 2,857,908 | 10/1958 | Cornfield | 128/15 |
| 2,897,624 | 8/1959 | Yakel et al. | 43/36 |
| 2,915,061 | 12/1959 | Edmondson et al. | 128/188 |
| 2,963,404 | 12/1960 | Hammer et al. | 167/82 |
| 3,172,179 | 3/1965 | Schafer | 24/91 |
| 3,192,924 | 6/1965 | Edmondson et al. | 128/188 |
| 3,264,115 | 8/1966 | Davis | 99/138 |
| 3,271,256 | 9/1966 | Frey | 167/82 |
| 3,341,414 | 9/1967 | Cherkas et al. | 167/82 |
| 3,399,673 | 9/1968 | Jones et al. | 128/188 |
| 3,418,743 | 12/1968 | Halvorsen | 43/35 |
| 3,556,811 | 1/1971 | Smith | 99/134 |
| 3,797,494 | 3/1974 | Zaffaroni | 128/268 |
| 3,816,953 | 6/1974 | Hameen-Anttila | 43/35 |
| 3,867,927 | 2/1975 | Hergott | 128/15 |
| 3,996,934 | 12/1976 | Zaffaroni | 128/268 |

(List continued on next page.)

OTHER PUBLICATIONS

Dyer Q. S. 1:4 Spring 1952 p. 18 "Medicated Candies"
Hug the Pharmacokinetics of Fentanyl, 9 pp. Janssen Pharmaceutica (1981).
Port et al., Cafentanil: The Primate Experience Oct. 1983 (2 pp.).
Dyer, "Medicated Candies" 1 Q.S. 4 (1953).
Dobkin, "Buprenorphine Hydrochloride: Determination of Analgesic Potency," 24 Canadian Anaesthesiology Society Journal 186 (1977).

(List continued on next page.)

Primary Examiner—Shep K. Rose
Attorney, Agent, or Firm—Workman, Nydegger & Jensen

[57] ABSTRACT

The present invention is directed to methods and compositions for noninvasively administering drugs having a sedative, analgesic, or anesthetic effect. A drug capable of absorption through mucosal tissues in incorporated into a candy matrix, which is then advantageously formed into a lollipop. A patient is put at ease when given the lollipop, and the drug rapidly enters the patient's bloodstream as the lollipop is sucked. When sedating or anesthetizing the patient, the physician can observe the patient's condition and remove the lollipop when it has had a desired effect on the patient. Alternatively, the physican can alter placement of the lollipop to slow the rate of the drug release for absorption into the patient's system. An analgesic-containing lollipop can be self-administrated by a patient in response to his own subjective experience of pain and to the patient's susceptibility to the particular drug utilized.

21 Claims, 2 Drawing Figures

U.S. PATENT DOCUMENTS

| | | | |
|---|---|---|---|
| 4,060,084 | 11/1977 | Chandrasekaran et al. | 128/260 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,139,627 | 2/1979 | Lano et al. | 424/361 |
| 4,346,709 | 8/1982 | Schmitt | 128/260 |
| 4,372,942 | 2/1983 | Cimilvca | 424/16 |
| 4,390,520 | 6/1983 | Hagai et al. | 424/28 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,485,087 | 11/1984 | Otsuka et al. | 424/28 |
| 4,551,329 | 11/1985 | Harris et al. | 424/22 |
| 4,588,580 | 5/1986 | Gale et al. | 424/21 |

OTHER PUBLICATIONS

Edge et al., "Analgesic Effects of Sublingual Buprenorphine," 34 Anaesthesia 463 (1979).

Fry, "Relief of Pain After Surgery," 34 Anaesthesia 549 (1979).

Bullingham et al., "Sublingual Buprenorphine Used Postoperatively: Clinical Observations and Preliminary Pharmacokinetic Analysis," 12 Br. J. Clin. Pharmac. 117 (1981).

Hug et al., "The Pharmacokinetics of Fentanyl," Janssen Pharmaceutica Inc. (1981).

Ellis et al., "Pain Relief After Abdominal Surgery—A Comparison of I. M. Morphine, Sublingual Buprenorphine and Self-Administered I.V. Pethidine," 54 Br. J. Anaesth. 421 (1982).

Port et al., "Carfentanil: The Primate Experience," American College of Veterinary Anesthesiologists (1983).

Port et al., "Topical Narcotic Anesthesia," 59 Anesthesiology (1983).

Bell et al., "Buccal Morphine—A New Route for Analgesia?" The Lancet 71 (1985).

"Sublimaze (fentanyl) as the Citrate Injection," Product Information (n.d.).

Brown, "Absorption of Analgesics from the Buccal Mucous Membrane," 196 The Practitioner 125 (1966).

Dearden et al., "Buccal Absorption as a Parameter of Analgesic Activity of Some p-Substituted Acetanilides," 23 Journal Pharm. Pharmac. 73S (1971).

Dearden et al., "A New Buccal Absorption Model," 23 J. Pharm. Pharmac. 68S (1971).

Beckett et al., "Buccal Absorption of Basic Drugs and its Application as an In Vivo Model of Passive Drug Transfer Through Lipid Membranes," 19 J. Pharm. Pharmac. 31S (1967).

Dollery et al., "Differences in the Metabolism of Drugs Depending Upon Their Routes of Administration," 179 Annals of the New York Academy of Sciences 108 (1971).

De Boer et al., "Drug Absorption by Sublingual and Rectal Routes," 56 British Journal of Anaesthesiology 69 (1984).

White et al., "Comparative Pharmacology of Intravenous Anesthetics—A Model for Determining Dosage Requirements and Therapeutic Concentration Ranges During Surgery," 59 Anesthesiology, A379 (Sep. 1983).

Stanley et al., "The Effect of Population Habits on Side Effects and Narcotic Requirements During High-Dose Fentanyl Anaesthesia," 31 Can Anaesth Soc J, 398 (1984).

Bailey et al., "Anesthetic Induction with Fentanyl," 64 Anesth Analg, 48 (1985).

Stanley et al., "Management of Pain and Pain-Related Problems in the Critically Ill Patient," Critical Care, State of the Art, vol. 6, (1985).

Stanley, "Computer Control of Intravenous Anesthesia," 423.

Schechter et al., "Status of Pediatric Pain Control: A Comparison of Hospital Analgesic Usage in Children and Adults" 77 Pediatrics 11 (1986).

Roberts et al., "Pharmacokinetics of Anaesthesia," Preface.

Bailey and Stanley, "Pharmacology of Intravenous Narcotic Anesthetics," in Anesthesia 2nd ed. (Miller ed. 1986).

USA Today, Jan. 28, 1986.

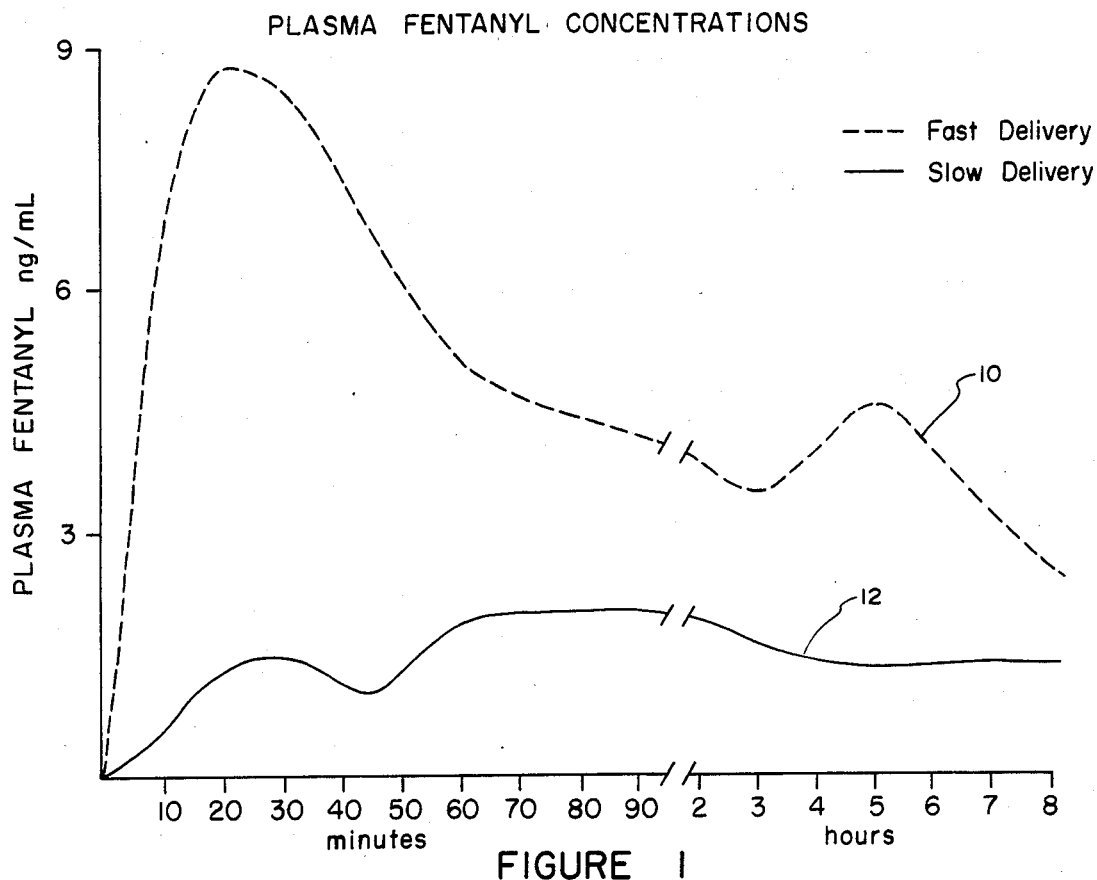
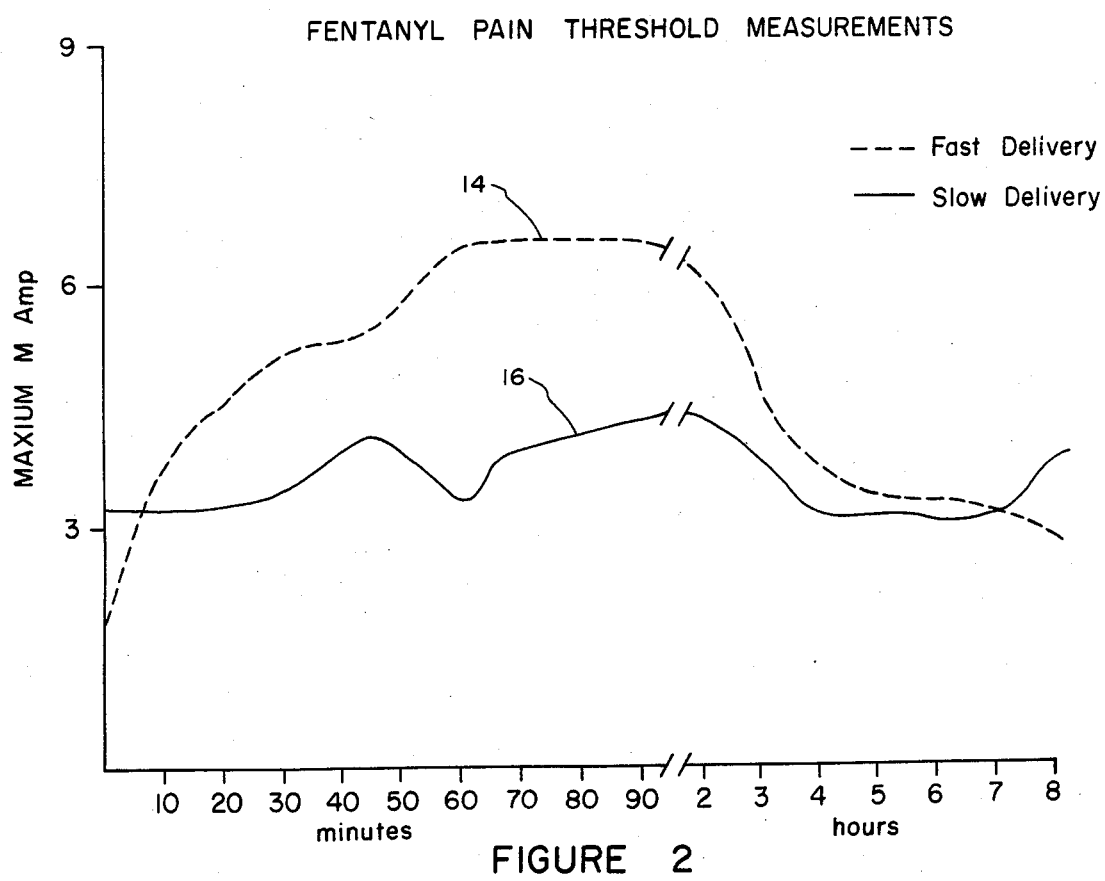

METHODS AND COMPOSITIONS FOR NONINVASIVE ADMINISTRATION OF SEDATIVES, ANALGESICS, AND ANESTHETICS

BACKGROUND

1. The Field of the Invention

The present invention is related to methods and compositions for use in delivering a pharmacological agent to a patient. More particularly, the present invention is directed to methods and compositions for noninvasive administration of pharmacological agents having sedative, analgesic, or anesthetic properties. 2. The Prior Art In recent years, a host of potent new drugs have become available for clinical use, and current expectations are that additional potent drugs will continue to become available in the future. In addition to treating specific diseases and conditions, physicians can prescribe drugs that will permit the physician to regulate many body functions and processes. Yet, despite the tremendous advances in the field of pharmacology, physicians continue to administer these new drugs using substantially the same techniques that have been employed for many decades.

Thus, almost all pharmacological agents continue to be administered via two routes, by mouth or by injection, despite the fact that both of these routes suffer from significant disadvantages in particular situations.

The simplest and most prevalent administration route is by mouth. To use this method, a pharmacological agent is incorporated into a tablet, a capsule, or into a liquid base. The patient then ingests an appropriate dose. Oral administration of a drug is extremely convenient, and for many drugs, it will continue to be the method of choice. Such administration is nonthreatening and is painless to the patient. For most patients, it is also very simple.

Nevertheless, oral administration of a drug suffers from the disadvantage that pediatric and geriatric patients frequently have difficulty swallowing pills, and such patients often refuse to cooperate in swallowing a liquid medication. Even more importantly, absorption of a drug into the bloodstream after swallowing a tablet varies from patient to patient. The absorption of the drug is dependent upon the movement from the stomach to the small and large intestines and the effects of secretions from these organs.

Moreover, there is often a substantial delay between the time of oral administration of a drug until it begins to have the desired therapeutic effect on the patient's system. Generally, a drug must pass from the stomach into the small and large intestines before it will be absorbed into the patient's bloodstream; unfortunately, this typically takes forty-five minutes or longer. For some applications, such a delay is unacceptable.

Further, many drugs taken orally are metabolized almost immediately—they are removed from or rendered ineffective by the patient's system before they can have any therapeutic effect. This occurs because the veins from the small and large intestines drain into the liver. Thus, drugs entering the patient's bloodstream through the intestines immediately pass through the patient's liver before distribution throughout the remainder of the patient's body. Unfortunately, upwards of sixty percent of a drug (and essentially one hundred percent of certain drugs) may be removed from the patient's bloodstream during this first pass through the liver; the result is that the oral route of administration is impractical for many drugs.

Yet a further difficulty encountered when administering drugs orally is that dosages are prepared or determined for use with an "average" patient. This is entirely acceptable for many drugs, but some drugs, such as those that have an effect on the patient's central nervous system, have a widely varying effect on different patients, depending upon individual variations in susceptibility to the particular drug utilized.

Underdosing a patient because of a low susceptibility to the drug fails to evoke the response sought by the physician. Overdosing the patient can result in dangerous depression of vital body functions. Moreover, the slow and uncertain response time for the onset of an observable reaction to a drug when taken orally makes it even more difficult to determine a proper dose for a particular patient; the physician may not learn for an hour whether the patient was underdosed or overdosed.

In order to avoid these serious disadvantages inherent in the oral administration route, physicians frequently resort to the injection route for administering many drugs. Injecting a drug (generally intravenously or intramuscularly) results in rapid entry of the drug into the patient's bloodstream; in addition, this type of delivery avoids the removal of large quantities of the drug by the patient's liver that accompanies oral administration. Rather, the drug becomes rapidly distributed to various portions of the patient's body before exposure to the liver; thus, the drug is removed by the liver at a substantially slower rate.

Unfortunately, most patients have at least some aversion to receiving injections. In some patients, this aversion may be so pronounced as to make the use of injections of serious concern to the physician. Since intense psychological stress can exacerbate a patient's debilitated condition, it sometimes becomes undesirable to use injections where the patient is seriously ill or suffers from a debilitating condition or injury.

To compound the problem facing a physician, the individual variation in susceptibility and metabolism with respect to various drugs, which makes it difficult to select an appropriate dose for oral administration is even more profound when utilizing the injection route. This is because smaller doses have an increased effect due to the rapidity in which the drug enters the bloodstream and because large portions of the drug are not immediately metabolized by the liver.

In order to prevent overdosing a patient with potent drugs, a prudent physician typically injects a patient with a lower than average dose, and later supplements the dose with additional injections as they appear necessary. This, of course, makes necessary the use of repeated injections, which in turn greatly increases the stress on the patient. It is not uncommon for a patient to come to fear that it is time for yet another injection every time the patient sees a member of the hospital staff, which is often the case for those most in need of potent drugs.

Considering these problems in medicament administration in light of a specific situation, one of the most difficult tasks facing a physician is preparing a patient psychologically for the rigors of a significant surgical operation and helping the patient through the painful period following surgery. Prior to an operation, it is frequently desirable to administer a drug having a sedative effect. Immediately prior to the operation, it is necessary to anesthetize the patient, and following the operation, it is necessary to administer an analgesic drug.

One common approach to preparing a patient for surgery is to administer a sedative orally. At this stage, quick onset of sedation is not critical; the drug can generally be administered well before its effect is required. Once the patient has been sedated, he is less fearful of injections. Following surgery, the level of pain is often so high that a patient may welcome injections of a fast-acting analgesic.

This is the approach which today is most widely practiced. It is generally successful in assisting a patient through the stress and discomfort of a surgical operation. Nevertheless, it also suffers from some serious disadvantages.

For example, a frightened child will often refuse to ingest a sedative; moreover, the inability to tolerate a potent drug may result in emesis shortly after taking a drug by oral administration. In either case, the child's level of stress will be significantly increased, and it will become even more difficult to elicit the child's cooperation with the physician and hospital staff. Subsequent resort to injections serves to reinforce the child's fears and increases the child's unwillingness to cooperate. It is not uncommon to find an adult patient who has had a traumatic experience of this type as a child, thereby resulting in severe anxieties or fears when facing surgery as an adult.

Another problem commonly arises during the postsurgical treatment of a patient with an analgesic. Pain is an extremely individual experience. Two persons undergoing the same surgical operation may have widely different subjective experiences of pain. Considering the individual experiences of pain as well as the individual variations in the susceptibility to the effects of an analgesic, it is very difficult for a physician to prescribe a suitable dose of analgesic for any particular patient. Again, the typical solution may be to prescribe an "average" dose, which may be too strong or too weak in any particular case. In an attempt to solve this problem, many physicians prescribe pain medication "on demand"; the patient is given pain medication substantially whenever he or she requests it.

As a patient begins to recover, his or her subjective experience of pain will eventually decrease to a point where it is no longer severe. If the patient is receiving pain medication by injection, a patient that has an aversion to injections will eventually reach the point where the act of administering the analgesic becomes stressful. Such a patient may choose to bear much unneeded pain rather than submit to additional injections. Refusing treatment with pain medication can actually reduce a patient's rate of recovery, as well as making the period of recovery more unpleasant for the patient and the hospital staff.

In view of the foregoing, it will be appreciated that it would be an important advancement in the art of administering drugs if suitable methods and compositions could be provided that were capable of rapid action and avoided the disadvantage of immediate metabolism through the patient's liver, yet did not involve injection.

It would also be an important advancement if methods and compositions could be provided that would give a physician control over the administration of medication so that a desired effect is obtained and maintained. It would be of further significant importance if methods and compositions could be provided that would permit a patient to easily control the amount of pain medication he or she receives according to his or her own subjective need for medication. Such methods and compositions are disclosed and claimed herein.

BRIEF SUMMARY AND OBJECTS OF THE INVENTION

The present invention is directed to novel methods and compositions for use in administering potent drugs capable of eliciting a sedative, analgesic, or anesthetic effect. The present invention is capable of introducing the drug into the patient's bloodstream almost as fast as an injection—and much faster than by the oral route. Yet, it is nonthreatening and painless.

These significant advantages are achieved by incorporating into a candy matrix a drug capable of being absorbed through the mucosal tissue found in a patient's mouth, pharynx and esophagus. The resultant mixture is then advantageously formed into a lollipop, which, as discussed in greater detail hereinafter, can be administered in a dose-to-effect manner.

Even patients that have difficulty swallowing a pill or refuse to swallow a liquid, will give little resistance to sucking on a lollipop. Particularly when dealing with children, a lollipop evokes a pleasurable response in the patient and gives the patient something nonthreatening on which to concentrate.

A sedative administered in this way will quickly enter the patient's bloodstream through the veins which serve the mucosal tissues, thereby serving to further lessen any remaining tension and fear. Appropriate monitoring of the patient's reaction to the drug will indicate when the drug has evoked a suitable response; the lollipop may then be removed, or its rate of consumption may be decreased. It will be appreciated that the ever-present risk of overdosing a patient is substantially minimized, if not almost eliminated, through the proper use of the methods and compositions within the scope of the present invention. The rate at which the drug is to be absorbed by the body can be varied by varying the rate the lollipop dissolves. Thus, the drug dose is given over a period of time rather than all at once, and the administration rate can be reduced if such appears necessary. If a patient should become too sedated, he will simply stop sucking the lollipop and/or the physician can easily remove the lollipop from the patient's mouth.

Following surgery, use of an analgesic-containing lollipop within the scope of the present invention allows extraordinary control over the amount to drug given to a patient. A patient can self-administer small amounts of drug "on demand" by simply licking or sucking on the lollipop in response to his subjective experience of pain.

Unlike the use of injections or oral ingestion of medication where a relatively large dose of medication is given intermittently, use of a lollipop can permit the patient to take very small doses of an analgesic drug on an almost continuous basis. Moreover, such administration can be regulated in response to the patient's own need for medication in light of his own subjective experience of pain and his own personal susceptibility to the particular drug utilized.

It is, therefore, a primary object of the present invention to provide noninvasive methods and compositions capable of rapidly inducing a state of sedation, analgesia, or anesthesia.

It is another important object of the present invention to provide methods and compositions that would allow for more physician control over the administration of a drug inducing a sedative, analgesic, or anesthetic effect so that individual patient differences in susceptibility and metabolism can be taken into account.

Yet another primary object of the present invention is to provide methods and compositions for drug administration which minimize the psychological trauma generally associated with injections and the adverse physical and psychological problems often associated with the oral administration of potent drugs.

It is a further object of the present invention to provide for methods of drug administration that are capable of dose-to-effect administration, thereby minimizing underdosing and overdosing of the patient.

Still a further object of the present invention is to provide methods and compositions that will permit a patient to control the amount of analgesic medication administered according to individual variations in the susceptibility to the particular medication used and in response to the patient's subjective experience of pain.

These and other objects and features of the present invention will become more fully apparent from the following description and appended claims taken in conjunction with the accompanying drawings.

BRIEF DESCRIPTION OF THE DRAWINGS

FIG. 1 is a graph showing the average plasma concentration of fentanyl in a group of subjects given fentanyl-medicated lollipops according to two delivery methods, one fast and one slow.

FIG. 2 is a graph of the pain-threshold measurements of the subjects whose fentanyl plasma concentrations are illustrated in FIG. 1.

DETAILED DESCRIPTION OF THE INVENTION

As discussed above, the present invention is directed to methods and compositions for use in the noninvasive administration of sedative, analgesic, and anesthetic agents. Advantageously, the present invention permits exceptional control over the effect of the drug administered, despite individual susceptibility to and metabolism of that drug.

While maintaining the convenience of oral administration, the present invention provides for the advantages of the injection route. At the same time, the present invention avoids the disadvantages identified above with respect to these two traditional routes of administration. The present invention achieves these results by utilizing yet a third administration route—absorption through mucosal tissues in the mouth and around the pharynx and esophagus.

A very few drugs, such as nitroglycerine, have historically been administered by absorption through mucous tissue because the transmucosal route is faster than oral administration, and unlike injections can be easily self-administered. While drugs are easily given by the transmucosal route, they have not, unfortunately, been given by a dose-to-effect method. In dose-to-effect drug administration, the drug is administered until a predetermined effect is obtained; thereafter the administration process is modified or terminated.

Despite some limited use, the transmucosal route has not been favored for routine use; instead, where a delay in drug action is acceptable, the oral route has been preferred by most physicians, and injections have been used where delay is not acceptable.

Transmucosal delivery of a drug is somewhat slower to provide active concentrations of a drug in a patient's system than is the use of an injection. Nevertheless, it has been discovered that the transmucosal route can be adapted so that any loss in the speed of drug uptake is more than offset by the ability to administer the drug noninvasively (much to the appreciation of the patient) and by the ability to control the dose received by the patient.

A drug must be lipophilic in order to be absorbed across mucosal tissue. However, this requirement is not a serious limitation since a large number of drugs are naturally lipophilic or can be provided in a lipophilic form.

In accordance with the present invention, a suitable drug is dispersed within a carbohydrate mass or other suitable matrix. The drug-containing carbohydrate mass is then given to a patient to suck on so that the drug will be released into the patient's mouth as the carbohydrate mass dissolves. Being lipophilic, a significant portion of the drug is absorbed through the mucosal tissues of the mouth and pharyngeal and esophageal areas. The drug rapidly enters the patient's bloodstream, and importantly, the blood in the veins draining from the mouth and the pharyngeal and esophageal areas passes through a substantial portion of the body (so that the drug can be absorbed) before the blood passes through the liver (where the drug may be inactivated).

The use of a carbohydrate matrix, or "candy," to administer a drug offers some important advantages, particularly when dealing with children. First, candy is familiar and lacks the menace of a syringe. Being a substance normally associated with pleasure, candy immediately evokes a positive psychological response.

Importantly, it has been found that the use of drug-containing candy in the form of a lollipop can permit the physician to control the dosage of the drug administered to the patient in order to produce a desired state of sedation or anesthesia, thereby resulting in dose-to-effect drug administration. Use of such drug-containing candy also permits the patient to exert control over the dosage received of an analgesic in order to diminish feelings of discomfort or pain.

These important advantages are available because very small amounts of drug may be delivered to a patient substantially continuously, and administration of the drug may be halted at any time by simply removing the candy from the patien's mouth. This not only allows a physician to monitor a patient's condition so that a particular effect is obtained and maintained, but also provides the important safety benefit. It is much less likely that a patient receiving medication in accordance with the dose-to-effect method of the present invention will become overdosed since the dose builds relatively slowly until a desired effect is achieved. Further, if a patient becomes slightly overdosed, it is likely that the patient will stop sucking the drug-containing lollipop before becoming seriously overdosed and/or the physician or other medical personnel will observe the situation and remove the lollipop.

In contrast, once a typically large dose of a drug is given orally or by injection, there is no retrieving it; thus, the full effects of the administered drug will be felt. Further, a large dose given every few hours results in wide swings in plasma concentration of the drug, while the use of a lollipop in accordance with the present invention evens out the plasma concentration of that drug.

In practice, a physician can offer the patient a piece of medicated candy on a stick, together with simple instructions that the candy is to be sucked rather than chewed. Children will particularly be put at ease by this approach. The physician can then monitor the patient's condition to ensure the desired effect is achieved. If, for example, the drug-containing candy contains a sedative, the physician can monitor the patient's condition until a suitable condition of sedation is achieved.

As mentioned above, it is preferred that the medicated candy take the form of a lollipop. Use of a stick or other suitable holder permits easy removal of the candy when a physician deems that a patient has received a proper dosage of the drug contained therein. Provision of a suitable holder also facilitates intermittent administration of drug to maintain a desired condition and makes it more convenient for a patient to intermittently self-administer an analgesic in respone to variations in the patient's subjective perception of pain.

The speed at which a sufficient amount of drug enters the patient's bloodstream so as to produce a desired effect depends on several factors. For example, a very potent drug requires fewer drug molecules to enter the patient's system than does a weak drug to produce a desired effect. Accordingly, if rapid onset of sedation, analgesia, or anesthesia is desired, a potent rather than a weak drug could be used.

Additionally, the degree of lipophilicity of a drug directly affects the rate of absorption of the drug. A highly lipophilic drug will result in the more rapid onset of a desired patient response than will a more moderately lipophilic drug. For example, fentanyl is a very potent drug which is highly lipophilic. However, sufentanil is nearly twice as lipophilic as fentanyl and thus is capable of faster absorption. It will be appreciated, however, that other pharmakinetic properties of a drug will affect the rate at which the effect of the drug is observed in the patient. For example, while alfentanil is not so lipophilic, its other pharmakinetic properties make it extremely fast acting once it is absorbed into the bloodstream.

The choices of matrix and the concentration of the drug in the matrix are also important factors with respect to the rate of drug uptake. A matrix that dissolves quickly will deliver drug into the patient's mouth for absorption more quickly than a matrix that is slow to dissolve. Similarly, a candy that contains drug in a high concentration will release more drug in a given period of time than a candy having a low drug concentration.

It will be appreciated that varying the concentrations of the drug in the matrix or the properties of the matrix (particularly the rate at which the matrix dissolves can be advantageously used in designing specific compositions for specific uses. A lollipop of a given concentration may be used to relieve the tension of the patient prior to surgery, while a lollipop of a stronger concentration (and preferably a different color so as to prevent confusion) may be used when it is desired to induce anesthesia. After surgery, a third lollipop where the matrix is comprised of a slower dissolving material may then be used to achieve the necessary analgesia.

Another use of these properties is to prepare a multilayer lollipop where the outer layer is of a concentration differing from that of the inner layer. Such a drug delivery system has a variety of applications. By way of example, it may be desirable to quickly get a predetermined dose of a drug into the bloodstream to obtain a desired effect and then use a different concentration to maintain that effect.

In addition to modifying the physical characteristics of the lollipop, the technique used by the patient to suck the lollipop may also be used to affect the rate of the absorption of the drug. If substantial portions of dissolved candy and drug are swallowed, the normal complications of oral administration will be encountered (i.e., slow response and loss of drug in the stomach and liver). If the candy is sucked slowly with little production of saliva, very little drug will be swallowed, but a reduction in the amount of saliva will also cause a reduction in the rate at which the medicated candy dissolves. It will be appreciated that the technique of sucking utilized can have a significant effect on the rate of drug uptake into the patient's bloodstream.

Use of a lollipop, in contrast to a simple drop or pellet, helps control proper placement of the candy within the patient's mouth since a physician or nurse can manipulate the candy in demonstrating proper placement to the patient, and the medical professional can easily monitor placement by observation of the angle of the protruding stick. Once a suitable technique for sucking the lollipop has been selected, the remaining factors can be adjusted accordingly.

It will be appreciated from the foregoing that the present invention has broad applicability to a variety of sedative, analgesic, and anesthetic agents. For example, the present invention may be utilized in the administration of narcotics such as morphine, fentanyl, sufentanil, lofentanil, carfentanil, and alfentanil; agonist-antagonist agents such as buprenorphine, pentacozine, and nalbuphine; phencyclidines such as ketamine; butorphanols such as droperidol and haloperidol; benzodiazepines such as valium, midazolam, and lorazepan; GABA stimulators such as etomidate; barbiturates such as pentathol and methohexitol, and barbiturate-like drugs such as deprivan; eugenols such as propanidid; and steroids such as minoxalone. It will be appreciated that other drugs may also be utilized within the scope of the present invention. What is important is that the drug be lipophilic and potent.

In incorporating a drug into a lollipop within the scope of the present invention, the amount of the drug used will generally differ from the amount used in more traditional injection and oral administration techniques. Depending upon the lipophilic nature of the drug, its potency, and its end use (sedation versus analgesia, versus anesthesia effect), the total concentration of the drug in a typical lollipop may contain from one to fifty times the amount of the drug which may be used in an injection. However, for purposes of example, Table I sets forth presently contemplated ranges of the dosages of certain drugs which would typically be used.

TABLE I

| Drug | Lollipop Dose Range |
| --- | --- |
| fentanyl | 500 micrograms–10 milligrams |
| sufentanil | 50–100 micrograms |
| lofentanil | 0.1–10 micrograms |
| carfentanil | 0.2–5 micrograms |
| methohexitol | 10–200 milligrams |
| buprenorphine | 100–400 micrograms |
| ketamine | 100–300 milligrams |
| droperidol | 1–5 milligrams |
| valium | 10–40 micrograms |
| midazolam | 5–25 milligrams |
| etomidate | 20–60 milligrams |
| minoxalone | 1–6 milligrams |
| deprivan | 5–20 milligrams |

The choice of a particular carbohydrate matrix is subject to wide variation. Conventional sweeteners such as sucrose may be utilized, or carbohydrates suitable for use with diabetic pateints, such as sorbitol or mannitol might be employed. Other sweeteners, such as the aspartanes, can also be easily incorporated into a composition in accordance with the present invention. The candy base may be very soft and fast dissolving, or may be hard and slower dissolving. Various forms will have advantages in different situations.

It will be appreciated from the foregoing that the present invention has broad applicability and will be useful in a wide variety of situations. It provides a useful alternative to the traditional oral and injection routes of administration, and permits the physician extraordinary control over the dosage of a sedative, analgesic, or anesthetic drug that is administered to a patient.

Some of the more important features and advantages of the present invention will be better appreciated and understood by reference to a few illustrative examples:

EXAMPLE 1

The candy matrix or base for drug-containing candy within the scope of the present invention is advantageously prepared utilizing candy preparation formulas and techniques which are known in the prior art. For example, a hard candy base is prepared by dissolving 50 grams of sucrose in 50 grams of water and heating the solution to about 240° F. Next, about 40 grams of corn syrup having a dextrose equivalent of 42 units, and a high maltose content (30%–35% maltose) is added, and the mixture is cooked at about 300° F. to reduce the water content to about three percent (3%). After re-cooling the thickened candy mass to about 240° F., a suitable oil flavoring (e.g., lemon or cherry) is added.

Concurrently, a solution containing a suitable drug is prepared for incorporation into a candy matrix. In this example, the drug selected is fentanyl. Fentanyl is a potent lipophilic drug useful as an analgesic and for sedating or anesthetizing a patient. Its high potency and lipophilicity make it an excellent drug for transmucosal administration in accordance with the present invention. A suitable fentanyl solution is prepared by dissolving 157 milligrams of fentanyl citrate (equivalent to 100 milligrams of fentanyl base) in 10 cubic centimeters of sterile water.

This fentanyl solution is mixed with 110 cubic centimeters of the hot candy mass formed as set forth above, and the resultant mixture is gently mixed as it cools to about 225° F., taking care not to induce formation of air bubbles in the candy mass.

The solution is then poured into suitable molds having a 6 cubic centimeter capacity that have been prelubricated with vegetable oil to prevent sticking. A four inch commercially available wax-coated compressed paper stick is next inserted into the base of each mold. The mixture is then permitted to set.

The foregoing procedure results in the preparation of twenty lollipops, each containing five milligrams of fentanyl equivalent. This dose is about 5 to 10 times higher than generally given by intravenous injection; a typical pediatric dose of fentanyl administered by injection is 500 micrograms, and a typical adult dose is about 1 milligram.

EXAMPLE 2

The procedure of this example shows the effect of varying the concentration of fentanyl in a medicated lollipop, and the effect of varying the rate at which a fentanyl-medicated lollipop is consumed.

Lollipops having one of two different dosages of fentanyl, (2 milligrams, 4 milligrams, and 5 milligrams, respectively, of fentanyl per lollipop) were prepared according to the general procedures of Example 1 above. The lollipops were administered to a total of 18 subjects. Approximately half of the individuals receiving each dosage were instructed to aggressively suck their lollipop in order to dissolve it as quickly as possible (e.g., in about five minutes). The remaining individuals were instructed to suck on the lollipop in a manner such that it would dissolve slowly (e.g., over a period of about an hour).

Table II summarizes the number of subjects involved in each test condition.

TABLE II

| DEMOGRAPHICS OF FENTANYL STUDY | | | |
|---|---|---|---|
| Speed of Administration | 5 mg lollipop | 4 mg lollipop | 2 mg lollipop |
| Fast | 4 | 1 | 4 |
| Slow | 3 | 2 | 4 |

Blood tests taken ten minutes after the patient was given a lollipop showed significant plasma concentrations of fentanyl in those subjects that aggressively sucked their lollipop, but only very slight traces in those subjects who were instructed to suck their lollipop slowly. Plasma concentrations of the subjects given the 4 milligram and 5 milligram dose lollipops are shown in Tables III and IV.

TABLE III

FIRST HOUR FENTANYL PLASMA CONCENTRATION
(nanograms/milliliter plasma)

| Subject Number | Fentanyl Dose (mg) | Delivery Method | Time (Minutes) | | | | |
|---|---|---|---|---|---|---|---|
| | | | 10 | 20 | 30 | 45 | 60 |
| 1 | 5 | Slow | <0.5 | 0.9 | — | 0.6 | 1.5 |
| 2 | 5 | Slow | <0.5 | 1.0 | 1.0 | 0.7 | 1.1 |
| 3 | 5 | Slow | <0.5 | 2.6 | 2.8 | 2.4 | 4.9 |
| 4 | 4 | Slow | <0.5 | 0.7 | 0.5 | 0.5 | 0.6 |
| 5 | 5 | Fast | 5.1 | 6.2 | 11.0 | 10.0 | 4.7 |
| 6 | 5 | Fast | 23.0 | 23.0 | 22.0 | 16.0 | 13.0 |
| 7 | 5 | Fast | 3.1 | 10.0 | 6.2 | 5.8 | 4.1 |
| 8 | 5 | Fast | 2.7 | 4.9 | 4.7 | 3.2 | 2.3 |
| 9 | 4 | Fast | 3.5 | 5.5 | 3.4 | 3.3 | 3.4 |
| 10 | 4 | Fast | 4.4 | 3.3 | 3.5 | 3.4 | 3.5 |

TABLE IV

SUSTAINED FENTANYL PLASMA CONCENTRATION
(nanograms/milliliter plasma)

| Subject Number | Fentanyl Dose (mg) | Delivery Method | Time (Hours) | | | | |
|---|---|---|---|---|---|---|---|
| | | | 1.5 | 2.0 | 3.0 | 5.0 | 8.0 |
| 1 | 5 | Slow | 1.5 | 1.7 | 0.9 | 1.3 | 1.0 |
| 2 | 5 | Slow | 1.1 | 0.8 | 0.6 | 0.5 | 0.5 |
| 3 | 5 | Slow | 4.6 | 5.1 | 3.9 | 3.1 | 3.4 |
| 4 | 4 | Slow | 0.9 | 0.7 | 0.5 | 0.5 | 0.8 |
| 5 | 5 | Fast | 5.1 | 5.2 | 5.8 | 13.0 | 7.5 |
| 6 | 5 | Fast | 10.0 | 7.2 | 6.2 | 6.1 | 3.4 |
| 7 | 5 | Fast | 2.9 | 2.9 | 3.6 | 2.1 | 0.8 |
| 8 | 5 | Fast | 1.9 | 2.1 | 1.8 | 2.2 | 1.1 |
| 9 | 4 | Fast | 3.6 | 3.0 | 2.7 | 2.8 | 1.1 |
| 10 | 4 | Fast | 2.7 | 3.0 | 2.6 | 1.9 | 0.6 |

A graph showing the mean plasma concentration of fentanyl is shown in FIG. 1, wherein line 10 represents the mean plasma concentration of subjects that aggressively sucked their lollipop, and line 12 represents the mean plasma concentration of those sucking their lollipop in a manner resulting in slow delivery of the drug.

It is noteworthy to observe that the plasma concentration of fentanyl administered relatively quickly, as represented by line 10, remains higher than the concentration of fentanyl administered more slowly, as represented by line 12, for several hours after lollipops taken by both methods have been completed. Accounting for this unexpected result can assist a physician to select a suitable administration technique for a particular use or situation.

The subjects of this study were also tested to quantify their subjective experience of pain before treatment and at various times after receiving a fentanyl-containing lollipop. Each subject was fitted with an electrode capable of delivering an electrical shock. Most patients were able to tolerate only about 2 to 3 milliamperes of current prior to treatment (a control range of 1.4 to 7.1 milliamperes was tolerated among the 18 subjects) but were able to tolerate up to 25 milliamperes, the maximum current level attempted, following treatment (a range of 2.1 to 25.0 milliamperes was tolerated following treatment).

FIG. 2 illustrates the mean pain-threshold measurements over time for the subjects involved in this study. Line 14 represents the pain threshold of those subjects that were instructed to suck their lollipop as quickly as possible, and line 16 represents the threshold measurements of those subjects instructed to suck their lollipops slowly for a more passive delivery.

Among the 18 subjects studied, the group had an average decrease in respiratory rate to about one-half of their pretest rate. One subject's respiratory rate dropped to such an extent that it was necessary to administer naloxone, a drug capable of counteracting the effect of a narcotic such as fentanyl. Some of the other subjects needed to be prompted to breathe from time to time, while others were less affected.

This example highlights the extremely wide variations in metabolism and subjective experience to pain from individual to individual. In view of these findings, it will be readily appreciated how difficult it is to administer a drug such as fentanyl to any particular individual with any confidence that such an individual will receive an appropriate dose.

Of course, the technique of administration used in this example involved each subject receiving an entire lollipop containing a particular dose of fentanyl. It is anticipated that in actual practice, a person would be given the lollipop until the appropriate effect is achieved. Thus, a person having a high susceptibility to the drug would not finish even one lollipop of the concentration used in this example, while those having a low susceptibility to the drug might be given a second lollipop to achieve a desired effect.

EXAMPLE 3

The procedure of this example illustrates the use of a sedative-containing lollipop in accordance with the present invention to prepare a child for outpatient surgery.

Outpatient surgery has become increasingly accepted as a cost-saving approach to many surgical procedures. Unfortunately, this approach does not give the physician and hospital staff much opportunity to place the patient at ease or let the patient become accustomed to his or her surroundings. Children are particularly uneasy and frightened when brought from their familiar and typically closely controlled home environment to the hustle and bustle and alien environment of a hospital.

It is, of course, desirable to make the outpatient visit as pleasant as possible. An important goal of the physician and staff is to minimize stress and discomfort while treating a patient's disease or condition. A relaxed and cooperative patient is also easier to work with.

It is very difficult to place a child at ease when arriving only a short time before surgery is to begin. Almost immediately the child is poked and prodded and forced to deliver up blood and urine samples. The child is then left in strange surroundings to brood and contemplate even worse things that may be about to happen to him.

Use of a sedative-containing lollipop in accordance with the present invention can do much to assist a patient in this situation through a very stressful period. Rather than give an oral medication, which is slow to act and uncertain in response, and rather than give an injection, which immediately makes a child distrustful and even more upset, the child is offered a lollipop.

The child's tension drops immediately as he or she turns his attention to the pleasant task of sucking the lollipop. Then, the calming influence of the sedative begins to take effect. Although a typical lollipop contains a drug dosage strong enough for children having even a low susceptibility to the drug, a physician or member of his staff will readily recognize the point where the child has received a suitable dose. A lollipop adapted for use in sedating a child might advantageously contain about 1 milligram of fentanyl.

At this stage, the medicated lollipop is taken from the child, perhaps to be replaced by a normal lollipop (preferably of a color readily distinguishable from the medicated lollipop). The child is then permitted additional "licks" of the medicated lollipop from time to time in order to maintain the desired level of sedation.

EXAMPLE 4

In the procedure of this example, a child is given a drug-containing lollipop in order to exert a sedative effect similar to the situation in Example 3. However, in this example, fentanyl in a lollipop dose of 3 milligrams is used, and the child is permitted to take a sufficient dose of medication so that he or she falls asleep.

As the child falls asleep, the drug-containing lollipop is removed and discarded. Not only is this approach very humane with respect to the child, but is also calming and reassuring to the child's parent who is able to observe the child go peacefully to sleep without the panic and noise so common with traditional approaches.

EXAMPLE 5

In the procedure of this example, an adult patient is given a drug-containing lollipop in order to exert sedative and anesthetic effects. However, in this example, fentanyl in a lollipop dose of 10 milligrams is used. The adult patient is permitted to take a sufficient dosage of the medication so that he or she falls asleep. The drug-containing lollipop is then removed and discarded.

EXAMPLE 6

In the procedure of this example, an adult patient is given a drug-containing lollipop in order to exert sedative and anesthetic effects similar to the situation in Example 5. However, in this example, sufentanil in a lollipop dose of 50 micrograms is used. The adult patient is permitted to take a sufficient dose of medication so that he or she falls asleep. The drug-containing lollipop is then removed and discarded.

EXAMPLE 7

In the procedure of this example, an adult is given a drug-containing lollipop in order to exert sedative and anesthetic effects similar to the situation in Example 5. However, in this example, methohexitol in a lollipop dose of 20 micrograms is used. The adult is permitted to take a sufficient dose of medication so that he or she falls asleep. The drug-containing lollipop is then removed and discarded.

EXAMPLE 8

The procedures of this example illustrate the use of an analgesic-containing lollipop in accordance with the present invention in order to treat pain.

As noted above, pain is an extremely personal experience. Two patients undergoing identical surgical procedures may have widely different experiences of post-operative pain. When taken together with the wide variation of different individual's responses to pain medication, it will be appreciated that it is very difficult for a physician to prescribe a suitable dose of pain medication in any particular situation.

An analgesic-containing lollipop in accordance with the present invention is ideally suited for use in this type of situation. In this example, a lollipop containing 0.5 milligrams of fentanyl is well-suited for analgesic use. A patient is given such a lollipop and invited to suck on it or "take a lick" as needed to control the pain.

Once the desired effect is achieved, the patient may place the lollipop passively in his mouth in order to obtain continuous low level administration of analgesic, and take an occasional "lick" if the passive route does not adequately keep up with the patient's need for medication. Regular supervision, as well as control over the number and frequency of lollipops provided will ensure that the patient does not self-administer an unacceptably high dose of analgesic.

The sense of control over his own condition, and the avoidance of stressful injections will assist a patient to a faster recovery.

EXAMPLE 9

In the procedure of this example, the procedure of Example 8 is used except that the lollipop contains 0.5 micrograms of lofentanil. Since this drug is well suited for analgesic use, the patient has control over the amount of pain experienced.

EXAMPLE 10

A drug-containing lollipop in accordance with the present invention is prepared substantially according to the procedure of Example 1, except that the drug buprenorphine in a lollipop dose of 0.2 milligrams is substituted for the fentanyl. The buprenorphine-containing lollipop is used in the procedures set forth in Examples 5 and 8.

EXAMPLE 11

A drug-containing lollipop in accordance with the present invention is prepared substantially according to the procedure of Example 1, except that the drug ketamine in a lollipop dose of about 40 milligrams is substituted for the fentanyl. The ketamine-containing lollipop is used in the procedures set forth in Examples 5 and 8.

EXAMPLE 12

A drug-containing lollipop in accordance with the present invention is prepared substantially according to the procedure of Example 1, except that the drug droperidol in a lollipop dose of about 20 milligrams is substituted for fentanyl. The droperidol-containing lollipop is used in the procedures set forth in Examples 5 and 8.

EXAMPLE 13

A drug-containing lollipop in accordance with the present invention is prepared substantially according to the procedure of Example 1, except that the drug valium in a lollipop dose of about 20 milligrams is substituted for fentanyl. The valium-containing lollipop is used in the procedures set forth in Examples 5 and 8.

EXAMPLE 14

A drug-containing lollipop in accordance with the present invention is prepared substantially according to the procedure of Example 1, except that the drug midazolam in a lollipop dose of about 10 milligrams is substituted for fentanyl. The midazolam-containing lollipop is used in the procedures set forth in Examples 5 and 8.

EXAMPLE 15

A drug-containing lollipop in accordance with the present invention is prepared substantially according to the procedure of Example 1, except that the drug etomidate in a lollipop dose of about 40 milligrams is substituted for fentanyl. The etomidate-containing lollipop is used in the procedures set forth in Examples 5 and 8.

EXAMPLE 16

A drug-containing lollipop in accordance with the present invention is prepared substantially according to the procedure of Example 1, except that the drug methohexitol in a lollipop dose of about 100 milligrams is substituted for fentanyl. The methohexitol-containing lollipop is used in the procedures set forth in Examples 5 and 8.

EXAMPLE 17

A drug-containing lollipop in accordance with the present invention is prepared substantially according to the procedure of Example 1, except that the drug minoxalone in a lollipop dose of about 3 milligrams is substituted for fentanyl. The minoxalone-containing lollipop is used in the procedures set forth in Examples 5 and 8.

EXAMPLE 18

A drug-containing lollipop in accordance with the present invention is prepared substantially according to the procedure of Example 1, except that the drug deprivan in a lollipop dose of about 10 milligrams is substituted for fentanyl. The deprivan-containing lollipop is used in the procedures set forth in Examples 5 and 8.

EXAMPLE 19

A drug-containing lollipop in accordance with the present invention is prepared substantially according to the procedure of Example 1, except that the drug carfentanil in a lollipop dose of about 0.2 milligrams is substituted for fentanyl. The carfentanil-containing lollipop is used as set forth in Examples 5 and 8.

From the foregoing, it will be appreciated that the present invention allows great flexibility and permits a physician control on a case-by-case basis with respect to the dose given to a particular patient, and the rate at which that dose is given.

The use of a drug-containing lollipop for administration of sedatives, analgesics, or anesthetic agents is much faster acting than oral administration, and also avoids unacceptable loss of drug on a first pass through the liver before systemic distribution. Further, the use of a lollipop in accordance with the present invention provides for a relatively level drug plasma concentration, which is preferable when dealing with sedatives and analgesics.

Further, a physician can easily monitor a patient's condition to ensure the patient receives a dose adequate to evoke a desired state of sedation or anesthesia. If necessary, the physician can instruct the patient to alter the aggressiveness with which he sucks the lollipop, or can take the lollipop from the patient.

A patient can also self-administer a suitable analgesic using a lollipop in accordance with the present invention. Thus, a patient can place an analgesic-containing lollipop passively in his mouth for continuous low level administration of a drug, or can take a lick of the lollipop from time to time as it may be needed to reduce his own subjective experience of pain.

Although the method and compositions of the present invention have been described with reference to specific examples, it is to be understood that the method and compositions of the present invention may be practiced in other forms without parting from its spirit or essential characteristics. The described methods and compositions are considered in all respects only as illustrative, and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method for administering the drug fentanyl in order to induce systemically a sedative, analgesic, or anesthetic effect, the method comprising the steps of:
   obtaining a soluble matrix material in the form of a lollipop into which the drug fentanyl has been dispersed, said soluble matrix material being capable of releasing the fentanyl for absorption through mucosal tissue;
   providing the drug-containing matrix to a patient to whom the fentanyl is to be administered in order to induce systemically the sedative, analgesic, or anesthetic effect;
   administering the drug-containing matrix in a manner such that said matrix is dissolved in the patient's mouth so that said is absorbed through mucosal tissue, thereby entering the patient's bloodstream, said administering step being accomplished in a dose-to-effect manner; and
   controlling the rate at which the drug-containing matrix is dissolved in order to obtain and maintain a desired effect.

2. A method for administering defined in claim 1, wherein the patient is initially caused to suck on the drug-containing matrix in a manner capable of effecting rapid dissolution thereof, such that relatively high quantities of drug are rapidly absorbed into the patient's bloodstream, so that the desired effect is obtained rapidly, and wherein the patient is thereafter caused to suck on the drug-containing matrix only as needed to maintain such desired effect.

3. A method for administering fentanyl as defined in claim 2, wherein the dosage of drug dispersed in the soluble matrix material is in the range of from about 1 to about 50 times greater than the dosage that would be given by intravenous injection.

4. A method for administering fentanyl as defined in claim 2, wherein the dosage of drug dispersed in the soluble matrix material is in the range of from about 5 to about 10 times greater than the dosage that would be given by intravenous injection.

5. A method for administering fentanyl as defined in claim 1, wherein the dosage of fentanyl dispersed in the matrix is from about 500 micrograms to about 10 milligrams of fentanyl equivalent.

6. A method for administering fentanyl as defined in claim 1, wherein the soluble matrix material is a carbohydrate mass.

7. A method for administering fentanyl as defined in claim 1, wherein the lollipop is intermittently removed from the patient's mouth in order to prevent an excessive amount of drug from being absorbed through mucous tissue into the patient's bloodstream.

8. A method for administering fentanyl as defined in claim 2, wherein the drug-containing matrix is maintained relatively passively in the patient's mouth after the desired effect is obtained in order to maintain such desired effect.

9. A method for administering systemically the analgesic drug fentanyl, comprising the steps of:
   obtaining a soluble matrix material in the form of a lollipop into which the drug fentanyl has been dispersed, said soluble matrix material being capable of releasing the fentanyl for absorption through musocal tissue;
   providing the drug-containing matrix to a patient to be treated with the analgesic drug; and
   administering systemically the drug-containing matrix in a manner such that said matrix is dissolved in the patient's mouth so that analgesic drug is absorbed through musocal tissue, thereby entering the patient's bloodstream, the patient controlling the rate of dissolution of the drug-containing matrix in a dose-to-effect manner in order to obtain and maintain a suitable level of relief from pain while accounting for the patient's individual susceptibility to the analgesic drug and the patient's individual subjective experience of pain.

10. A method for administering fentanyl as defined in claim 9, wherein the soluble matrix material is a carbohydrate mass.

11. A method for administering fentanyl as defined in claim 9, wherein the lollipop is intermittently removed from the patient's mouth in order to prevent an excessive amount of drug from being absorbed through mucosal tissue into the patient's bloodstream.

12. A method for administering fentanyl as defined in claim 9, wherein the lollipop is sucked on substantially continuously in a passive manner so that relatively small quantities of analgesia enter the patient's bloodstream substantially continuously, and wherein the patient increases the aggressiveness of such sucking in response to increases in the experience of pain so as to increase the quantity of drug entering the patient's bloodstream in order to provide relief from such increases in pain.

13. A method for administering fentanyl as defined in claim 9, wherein the dosage of drug dispersed in the soluble matrix is in the range of from about 1 to about 50 times greater than the dosage that would be given by intravenous injection.

14. A method for administering fentanyl as defined in claim 9, wherein the dosage of drug dispersed in the soluble matrix is in the range of from about 5 to about 10 times greater than the dosage that would be given by intravenous injection.

15. A method for administering fentanyl as defined in claim 9, wherein the dosage of fentanyl dispersed in the matrix is from about 500 micrograms to about 10 milligrams of fentanyl equivalent.

16. A composition for use in systemically inducing a sedative, analgesic or anesthetic effect in a patient, said composition comprising:
   an effective dose of the drug fentanyl in a form capable of being absorbed through mucosal tissue, and capable of systemically inducing a condition of sedation, analgesia, or anesthesia in a patient;
   a soluble matrix material, the fentanyl being dispersed substantially uniformly within the matrix so that the drug is released for absorption through mucosal tissue as the matrix dissolves when placed in a patient's mouth; and
   holder means secured to the drug-containing matrix, said holder means being configured so as to permit convenient insertion of the drug-containing matrix into the mouth of a patient, and convenient removal thereof when a desired condition is obtained.

17. A composition as defined in claim 16, wherein the holder means is a stick.

18. A composition as defined in claim 16, wherein the dosage of drug dispersed in the soluble matrix material is in the range of from about 1 to about 50 times greater than the dosage that would be given by intravenous injection.

19. A composition as defined in claim 16, wherein the dosage of drug dispersed in the soluble matrix material is in the range of from about 5 to about 10 times greater than the dosage that would be given by intravenous injection.

20. A composition as defined in claim 16, wherein the drug is fentanyl and the dosage of fentanyl dispersed in the matrix is from about 500 micrograms to about 10 milligrams of fentanyl equivalent.

21. A composition as defined in claim 16, wherein the drug-containing matrix is in the form of a lollipop.

* * * * *

UNITED STATES PATENT AND TRADEMARK OFFICE
CERTIFICATE OF CORRECTION

PATENT NO. : 4,671,953
DATED : June 9, 1987
INVENTOR(S) : Theodore H. Stanley and Brian Hague Page 1 of 2

It is certified that error appears in the above-identified patent and that said Letters Patent are hereby corrected as shown below:

Title Page, Col. 1, under "Inventor": "Brian Haque" should be --Brian Hague--

Col. 1, line 14, "2. The Prior Art" should be a new section heading

Col. 2, line 44, "administration is" should be -- administration, is --

Col. 5, line 52, "nitroglycerine" should be -- nitroglycerin --

Col. 6, line 46, "patien's" should be -- patient's --

Col. 8, line 36, "methohexitol" should be -- methohexital --

Col. 8, line 60 (Table I), "methohexitol" should be -- methohexital --

Col. 9, line 6, "aspartanes," should be -- aspartames, --

Col. 10, lines 3-4, "two" should be -- three --

Col. 13, line 8, "methohexitol" should be -- methohexital --

UNITED STATES PATENT AND TRADEMARK OFFICE
CERTIFICATE OF CORRECTION

PATENT NO. : 4,671,953
DATED : June 9, 1987
INVENTOR(S) : Theodore H. Stanley and Brian Hague It is certified that error appears in the above-identified patent and that said Letters Patent are hereby corrected as shown below:

Col. 13, line 22, "individual's" should be -- individuals' --

Col. 14, lines 39-40, "methohexitol" should be -- methohexital --

Col. 15, line 56 (claim 1), "said is" should be -- drug is --

Col. 15, line 63 (claim 2), "administering defined" should be
-- administering fentanyl as defined --

Signed and Sealed this

Twenty-second Day of December, 1987

Attest:

DONALD J. QUIGG

*Attesting Officer*          *Commissioner of Patents and Trademarks*